United States Patent
Lee et al.

(10) Patent No.: US 10,338,059 B2
(45) Date of Patent: Jul. 2, 2019

(54) LUNG MODEL DEVICE FOR INHALATION TOXICITY TESTING

(71) Applicant: KOREA RESEARCH INSTITUTE OF CHEMICAL TECHNOLOGY, Daejeon (KR)

(72) Inventors: Kyu Hong Lee, Jeongeup-si (KR); Hyo Seon Yang, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 138 days.

(21) Appl. No.: 15/322,894

(22) PCT Filed: Jun. 4, 2015

(86) PCT No.: PCT/KR2015/005615
§ 371 (c)(1),
(2) Date: Dec. 29, 2016

(87) PCT Pub. No.: WO2016/003079
PCT Pub. Date: Jan. 7, 2016

(65) Prior Publication Data
US 2017/0160268 A1    Jun. 8, 2017

(30) Foreign Application Priority Data
Jul. 1, 2014   (KR) .................. 10-2014-0081774

(51) Int. Cl.
C12M 1/34       (2006.01)
G01N 33/50      (2006.01)
C12M 1/00       (2006.01)

(52) U.S. Cl.
CPC ......... *G01N 33/5014* (2013.01); *C12M 23/00* (2013.01); *G01N 33/5044* (2013.01)

(58) Field of Classification Search
CPC ...... C12M 21/08; C12M 23/26; C12M 23/36; C12M 25/02; C12M 25/14; G01N 33/5014; G01N 33/5044
See application file for complete search history.

(56) References Cited

U.S. PATENT DOCUMENTS
2012/0219985 A1    8/2012  Yoon et al.

FOREIGN PATENT DOCUMENTS
JP    2014-102186 A      6/2014
KR    10-2012-0102180 A  9/2012
KR    10-1221106 B1      1/2013

OTHER PUBLICATIONS

Kelly BéruBé et al., "In Vitro Models of Inhalation Toxicity and Disease", Alternatives to Laboratory Animals 37, pp. 89-141, Feb. 2009.

*Primary Examiner* — William H. Beisner
(74) *Attorney, Agent, or Firm* — Rabin & Berdo, P.C.

(57) ABSTRACT

A lung model device for inhalation toxicity testing is provided. The device has a plurality of mesh tissue panels having lung cells attached thereto arranged inside a case so as to have a similar structure to a human lung, and air and nanoparticles are supplied into the case through a separate respiratory operating unit, thereby enabling inhalation toxicity testing on nanoparticles to be simply and conveniently performed in an indirect way by determining changes in the state of the lung cells without using real laboratory animals. The mesh tissue panels having a smaller lattice spacing size are sequentially positioned according to the nanoparticle inflow direction, thereby providing a structure similar to the structure of a real lung.

20 Claims, 5 Drawing Sheets

LUNG MODEL DEVICE FOR INHALATION TOXICITY TESTING

TECHNICAL FIELD

Figure 1:
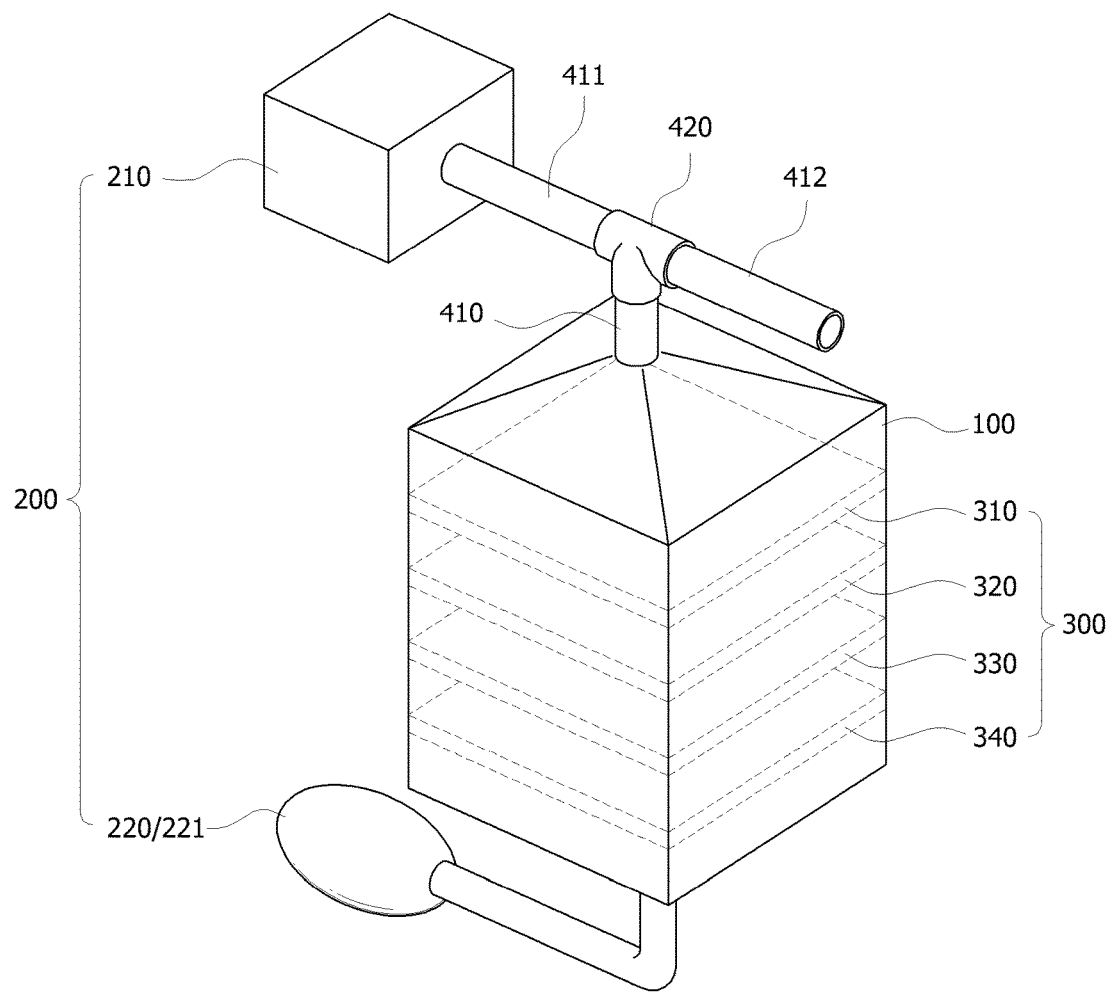

The present disclosure relates to a lung model device for inhalation toxicity testing, and more particularly, to a lung model device for inhalation toxicity testing, capable of simply and conveniently performing an inhalation toxicity test on nanoparticles through an indirect method of determining a change in a state of a lung cell without using an actual laboratory animal to thereby replace general nanoparticle inhalation toxicity testing devices, by arranging a plurality of mesh tissue panels in a case to have a structure similar to a structure of human lungs and supplying air and nanoparticles to the case through a separate respiratory operating unit, realizing a structure similar to a structure of an actual lung to thereby improve accuracy of inhalation toxicity testing without using the laboratory animal, by arranging a plurality of mesh tissue panels such that mesh tissue panels are sequentially located in an internal space of the case in an inflow direction of nanoparticles in descending order of lattice spacing sizes thereof, the lung cell being attached to the plurality of mesh tissue panels.

BACKGROUND ART

The twentieth century may have been the "micro" century, but the twenty-first century will be the "nano" century. In this regard, nanotechnology may be mainly classified into nano material technology, nano device technology, environmental and biotechnology, and the like.

Nanotechnology is a technology for producing a material or a device having new properties or functions by artificially modifying an ultrafine material on the atomic or molecular scale. Recently, nanotechnology has emerged as a leading-edge technology for realizing information technology (IT) and biotechnology (BT) devices.

Nanotechnology is forecast to provide sufficient benefits and advantages to be recognized as a new technological revolution in various industries. However, nanotechnology is well known to have potential risks, risks caused by properties of nanotechnology themselves.

That is, as a size of a particle is decreased, a specific surface area thereof may be increased. As described above, when a particle having a greater specific surface area reacts with a biological tissue, the toxicity thereof is increased. For example, it has been proved by experimentation that various types of nanoparticles, such as titanium dioxide particles, carbon powder particles, and a diesel exhaust particles can cause inflammation (of the lungs), and may have higher toxicity as a size thereof is reduced. In addition, an ultrafine particle may be deeply lodged in a lung cell or may be transported to the brain in a state of not having been filtered by an airway or a mucous membrane. Furthermore, several recent studies have shown that nanoparticles may cause diseases, and even central nervous system lesions.

Recently, with the development of nanotechnology, stability evaluation of nanotechnology has also been actively performed, and representatively, an inhalation toxicity test on nanoparticles has been undertaken with various laboratory animals, the inhalation toxicity test evaluating toxicity generated when nanoparticles are inhaled and accumulated in a human body. Data relating to nanoparticle harmfulness to the human body acquired through inhalation toxicity tests on nanoparticles is used as base data relating to nanoparticles in the manufacturing of products such as nanofibers, cosmetics, semiconductors, and drug carriers across a range of industrial sectors.

Recently, as the importance of nanotechnology has come to the fore, in addition to inhalation toxicity tests on the nanoparticles, various other tests, such as an effectiveness tests on the nanoparticles with respect to the human body, stability tests on nanoparticles, and environmental effect evaluations of nanoparticles have been conducted. Since the various tests are mostly conducted in the same manner as the inhalation toxicity test, in that the various tests all evaluate an influence of nanoparticles on the human body, such tests on nanoparticles will be collectively known as an inhalation toxicity test below.

In addition, since nanoparticles can exist in an aerosol state and a test on nanoparticles is equally applied to particles having a submicron particle diameter and existing in the aerosol state, the term nanoparticles will be used in the sense of including submicron particles below, unless otherwise specified.

Since the nanoparticles have a very fine size, nanoparticles may directly move deep inside a lung and may be attached to lung tissue during human respiration. Therefore, inhalation toxicity tests on nanoparticles are generally performed through a method of generating nanoparticles in an aerosol state, supplying the nanoparticles to an exposure chamber having a certain size, introducing a laboratory animal into the exposure chamber, exposing the laboratory animal to the nanoparticles, and subsequently measuring various changes in the state of the laboratory animal.

That is, the inhalation toxicity test on the nanoparticles is performed through a method of exposing the laboratory animal to nanoparticles, allowing the nanoparticles to be inhaled deep inside the lungs of the laboratory animal, attaching the nanoparticles to the lungs, and subsequently measuring a change in a health condition of the laboratory animal.

The aforementioned inhalation toxicity test should be performed by using the laboratory animal. Recently, since ethical problems with respect to an animal testing have come to the fore, regulations have been continuously increased on testing using laboratory animals. In addition, since lung model devices for inhalation toxicity testing have a large scale and a complex structure, while installation and operation costs thereof are high, there are limitations on the use thereof, in that it may not be easy to gain ready access to lung model devices.

DISCLOSURE

Technical Problem

The present disclosure has been made in consideration of the above-described problems occurring in the related art, and the present disclosure proposes a lung model device for inhalation toxicity testing, capable of simply and conveniently performing an inhalation toxicity test on nanoparticles through an indirect method of determining a change in a state of a lung cell without using an actual laboratory animal to thereby replace general nanoparticle inhalation toxicity testing devices, by arranging a plurality of mesh tissue panels in a case so as to have a structure similar to a structure of human lungs and supplying air and nanoparticles to the case through a separate respiratory operating unit, the lung cell being attached to the plurality of mesh tissue panels.

Also proposed is a lung model device for inhalation toxicity testing, capable of realizing a structure similar to a structure of an actual lung to thereby improve accuracy of an inhalation toxicity test without using a laboratory animal, by arranging a plurality of mesh tissue panels such that mesh tissue panels are sequentially located in the inflow direction of the nanoparticles in descending order of lattice spacing sizes thereof.

Figure 2:
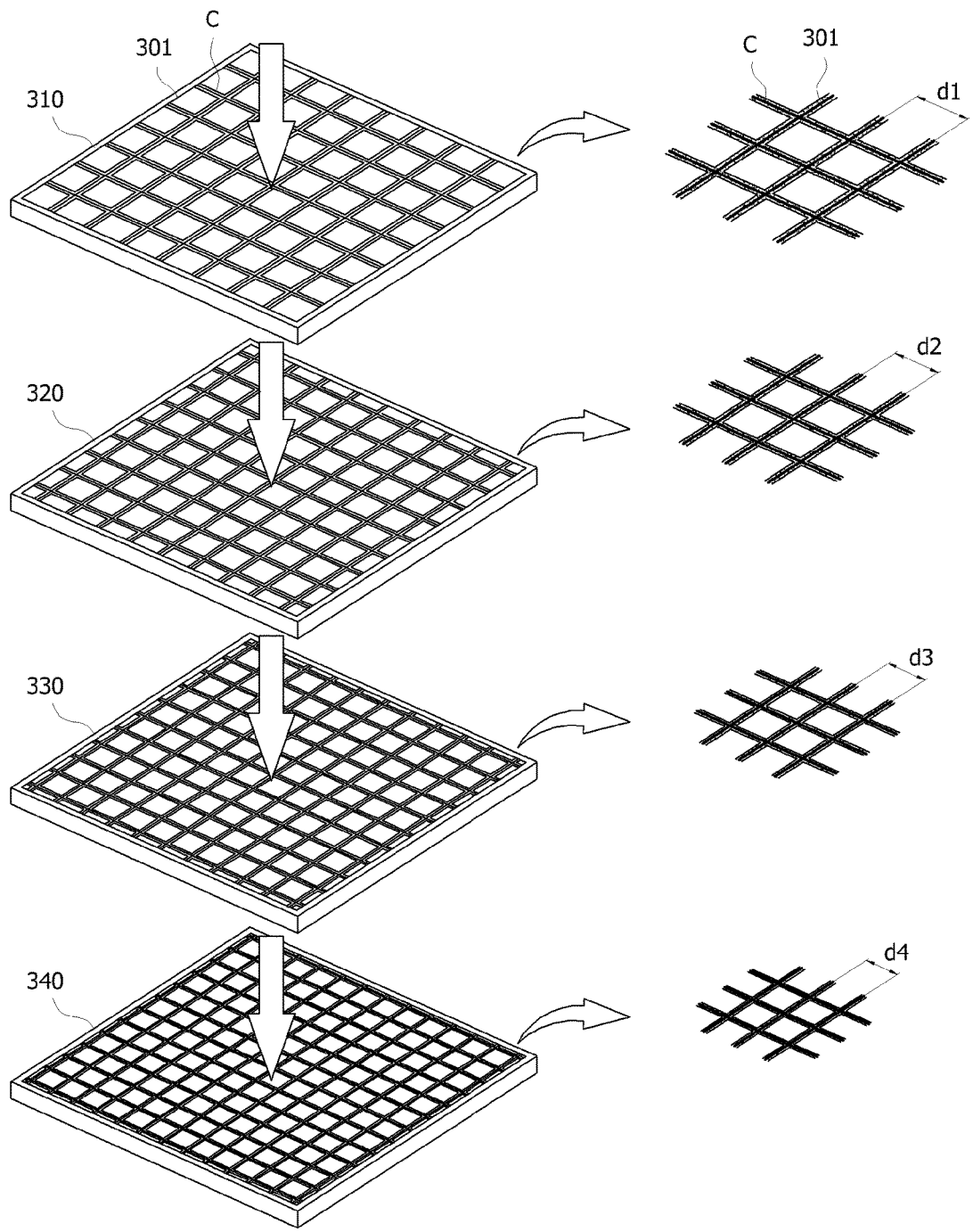
Figure 3:
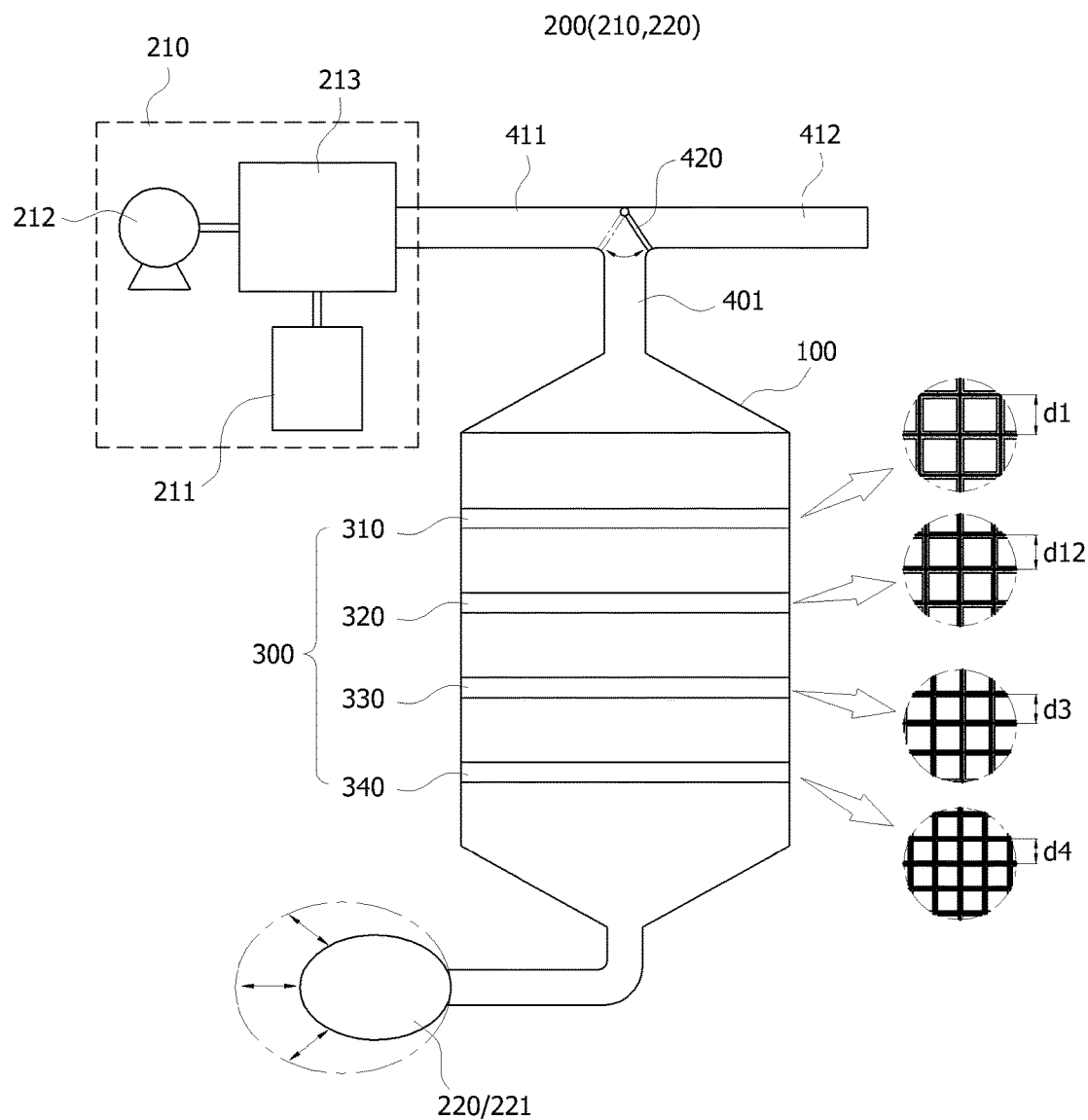
Figure 4:
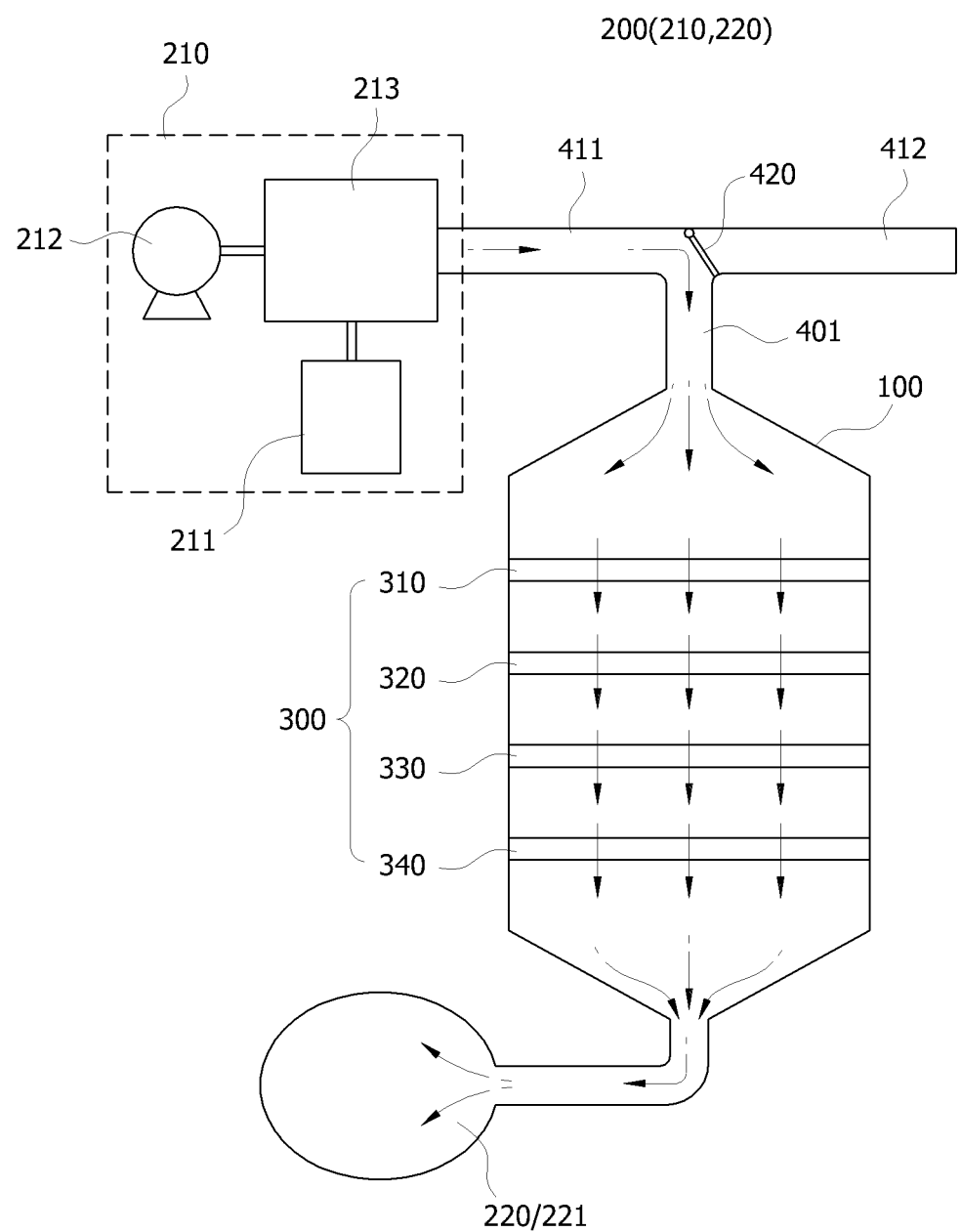
Figure 5:
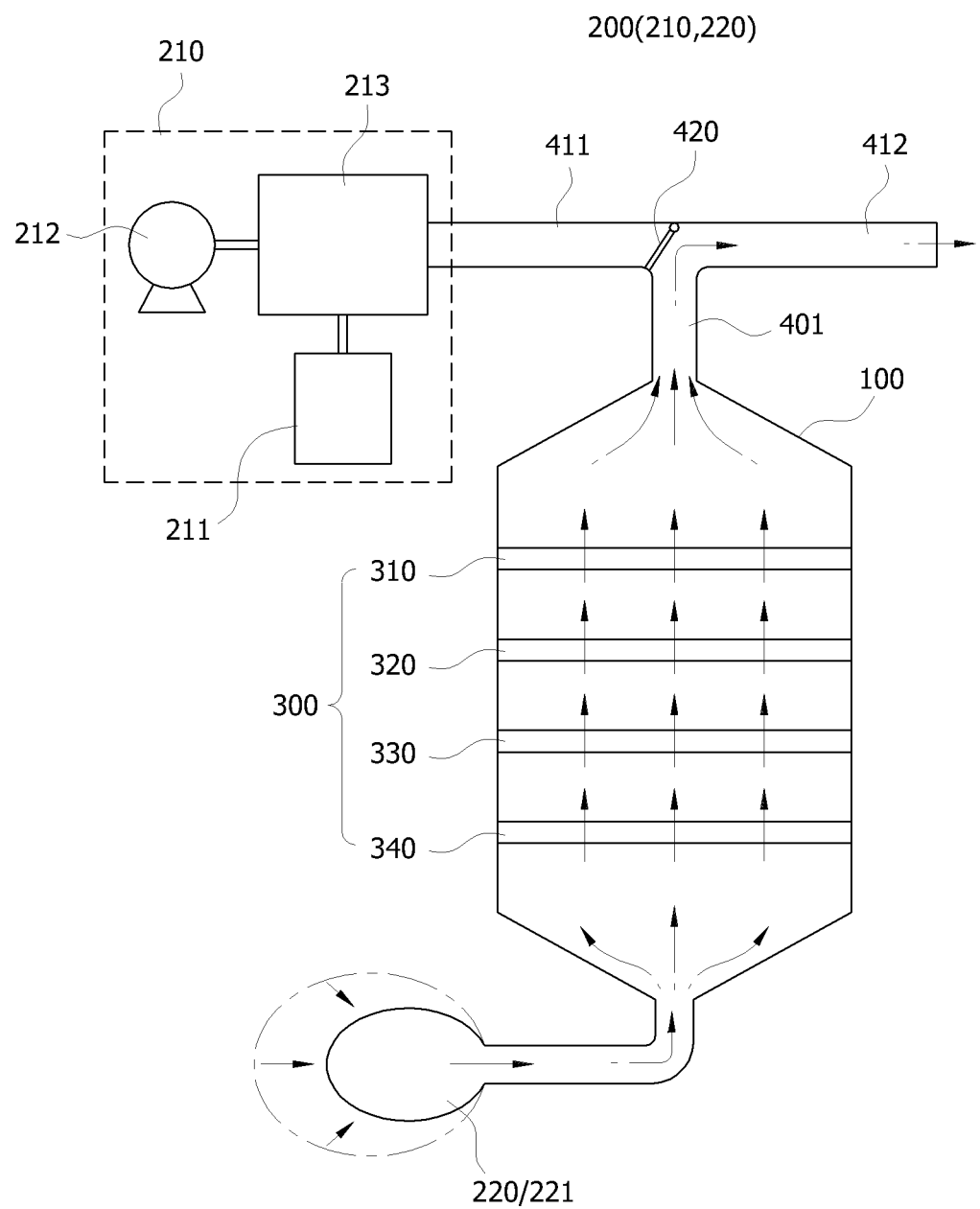

Technical Solution $ According to an aspect of the present disclosure, a lung model device for inhalation toxicity testing may include: a case having an internal space formed therein; an inhalation operating unit allowing air and nanoparticles to flow into the internal space of the case by alternately and repeatedly performing an inflow operation and a discharge operation on the air with respect to the internal space of the case; and mesh tissue panels mounted in plural in the internal space of the case, having different lattice spacings, and having lattice lines to which lung cells of a human or an animal are attached, wherein the plurality of mesh tissue panels are sequentially arranged in the internal space of the case in an inflow direction of the nanoparticles in descending order of sizes of the different lattice spacings thereof.

At this time, the respiration operating unit may include: a particle supply module allowing nanoparticles and air to flow into the internal space of the case by generating the nanoparticles; and an air discharge module discharging air from the internal space of the case, wherein the particle supply module and the air discharge unit alternately and repeatedly operate.

In addition, the particle supply module may include: a particle generator generating nanoparticles; and an air inflow pump allowing air to flow into the internal space of the case such that the nanoparticles generated by the particle generator flow into the internal space of the case together with the air.

Further, the air discharge module may include a buffer bag communicating with the internal space of the case such that the air flowing into the internal space of the case through the particle supply module passes through the plurality of mesh tissue panels 300, and then, flows into the buffer bag, wherein the buffer bag is formed of an elastic material such that a shape thereof is restored, and the air flowing into the internal space of the case is discharged from the internal space of the case by elastic restoring force of the buffer bag.

Furthermore, the air discharge module may include: a buffer bag communicating with the internal space of the case such that the air flowing into the internal space of the case through the particle supply module passes through the plurality of mesh tissue panels, and then, flows into the buffer bag; and an air discharge pump discharging air from the internal space of the case.

In addition, a main pipe may be mounted in the case to communicate with the internal space such that air flows into and from the internal space, and may be branched into an inflow pipe and a discharge pipe, wherein the inflow pipe is connected to the particle supply module such that the air and the nanoparticles flow into the internal space of the case, and the discharge pipe is formed to have an open end such that air is discharged from the internal space of the case.

Further, a channel conversion valve may be mounted at a branched portion of the main pipe to selectively open the inflow pipe and the discharge pipe, and may operate in a state of being interlocked with an operating state of the particle supply module and an operating state of the air discharge nodule.

Furthermore, the plurality of mesh tissue panels may be formed such that the lung cells of the human or the animal are uniformly cultivated on the lattice lines of each of the plurality of mesh tissue panels.

In addition, the plurality of mesh tissue panels may be provided as at least four mesh tissue panels having different lattice spacings, and a trachea cell, a bronchial tube cell, a bronchial branch cell, and an alveolus cell of the lung cells in the human or the animal may be respectively cultivated on the at least four mesh tissue panels having different lattice spacings.

Advantageous Effects

As set forth above, according to the present disclosure, an inhalation toxicity test on nanoparticles may be simply and conveniently performed through an indirect method of determining a change in a state of a lung cell without using an actual laboratory animal to thereby replace general nanoparticle inhalation toxicity testing devices, by arranging a plurality of mesh tissue panels in a case so as to have a structure similar to a structure of human lungs and supplying air and nanoparticles to the case through a separate respiratory operating unit, the lung cell being attached to the plurality of mesh tissue panels.

In addition, a structure similar to a structure of an actual lung may be realized to improve accuracy of the inhalation toxicity test without using a laboratory animal, by arranging the plurality of mesh tissue panels such that mesh tissue panels are sequentially located in an internal space of the case in an inflow direction of the nanoparticles in descending order of lattice spacing sizes thereof.

DESCRIPTION OF DRAWINGS

FIG. 1 is a schematic perspective view illustrating an appearance of a lung model device for inhalation toxicity testing according to an embodiment of the present disclosure.

FIG. 2 is a schematic view illustrating a placement state of mesh tissue panels according to an embodiment of the present disclosure.

FIG. 3 is a schematic cross-sectional view illustrating an inner structure of a lung model device for inhalation toxicity testing according to an embodiment of the present disclosure.

FIGS. 4 and 5 are schematic views illustrating an operating state of a lung model device for inhalation toxicity testing according to an embodiment of the present disclosure.

MODE FOR INVENTION

Hereinafter, an exemplary embodiment of the present disclosure will be described in detail with reference to the accompanying drawings. In the following description, the same elements will be designated by the same reference numerals although they are shown in different drawings. Further, in the following description, detailed descriptions of well-known functions or constructions will be omitted since they would obscure the present disclosure in unnecessary detail.

FIG. 1 is a schematic perspective view illustrating an appearance of a lung model device for inhalation toxicity testing according to an embodiment of the present disclosure, FIG. 2 is a schematic view illustrating a placement state of mesh tissue panels according to an embodiment of the present disclosure, FIG. 3 is a schematic cross-sectional view illustrating an inner structure of the lung model device for the inhalation toxicity testing according to the embodiment of the present disclosure, and FIGS. 4 and 5 are schematic views illustrating an operating state of the lung model device for the inhalation toxicity testing according to the embodiment of the present disclosure.

The lung model device for the inhalation toxicity testing according to the embodiment of the present disclosure is a lung model device capable of replacing an inhalation toxicity testing device using a laboratory animal, and performing an inhalation toxicity test on nanoparticles without using an actual laboratory animal.

First, regarding a structure and a function of human lungs, human lungs have a semi-conical shape as a whole and include a left lung and a right lung. The left lung and the right lung face each other with a vertical partition therebetween and occupy most of the thoracic cavity. The right lung is divided into three lobes, i.e., upper, middle, and lower lobes, and the left lung is divided into two lobes, i.e., upper and lower lobes.

The lung is responsible for a respiration function and the left lung and the right lung are each connected to a trachea. The trachea is divided into a left trachea and a right trachea at the height of the fifth thoracic vertebra and enters the lung through each hilum. A bronchial tube is divided into lobar bronchi at the hilum, and is branched into bronchioles from bronchial branches in the lung to become thinner. Finally, the bronchial tube forms a cystoid alveolus. That is, countless follicles known as alveoli are gathered to form a substance of the lungs. Capillary plexus closely surround the countless alveoli and exchange gas with red blood cells through the alveoli.

During human respiration, in an inhalation process, air enters the lung through an airway and the trachea and reaches the bronchial tube, the bronchial branch, and the alveolus. Nanoparticles in air in the inhalation process may be inhaled deep inside the human lungs. The trachea, the bronchial tube, the bronchial branch, and the alveolus sequentially constitute more fine tissues. Generally, since particles having a large diameter are attached to the trachea, the bronchial tube, or the like, particles having a large diameter are not inhaled deep inside the lung. However, particles such as nanoparticles having a very fine size may be inhaled into the bronchial branch and the alveolus.

An inhalation toxicity test on nanoparticles is performed through a method of allowing nanoparticles to be inhaled deep inside a lung of a laboratory animal through respiration and determining a change in a health condition of the laboratory animal due to the inhalation of nanoparticles.

The lung model device for inhalation toxicity testing according to the embodiment of the present disclosure is a device capable of performing an inhalation toxicity test on nanoparticles without the use of a laboratory animal by allowing nanoparticles to be inhaled through a respiration method using a structure similar to a structure of the human lungs. The lung model device for inhalation toxicity testing includes a case 100, a respiration operating unit 200, and mesh tissue panels 300.

The case 100 may have a shape having an accommodation space (internal space) formed therein and may be formed to have a general box shape. Since an air flow is generated inside of the case 100 by the respiration operating unit 200 to be described later, in order for the air flow to be smoothly performed, the case 100 may be formed such that the internal space thereof forms a cylindrical shape or may be formed to have various shapes such as a square pillar shape or a polygonal pillar shape, as illustrated in FIG. 1.

The respiration operation unit 200 is configured such that a respiration operation is performed through a method of alternately and repeatedly performing an air inflow and discharge operation with respect to the internal space of the case 100. In addition, the respiration operation unit 200 is configured such that nanoparticles flow into the internal space together with air through the respiration operation. The respiration operating unit 200 may include a particle supply module 210 allowing the nanoparticles and the air to flow into the internal space of the case 100 by generating the nanoparticles and an air discharge module 220 discharging air from the internal space of the case 100. An inhalation function of the respiration operation is performed by the particle supply module 210 and an expiration function of the respiration operation is performed by the air discharge module 220.

The mesh tissue panels 300 are formed in a mesh lattice form and are mounted in the internal space of the case 100, and a lung cell C of a human or an animal is attached to each of lattice lines 301. One or more mesh tissue panels 300 may be mounted in the internal space of the case 100. However, it is desirable that a plurality of mesh tissue panels 300 be mounted to have a structure similar to a structure of an actual lung in the human or the animal.

The plurality of mesh tissue panels 300 (310, 320, 330, and 340) are formed to have different lattice spacings $d_1$, $d_2$, $d_3$, and $d_4$ as illustrated in FIGS. 2 and 3. The mesh tissue panels 300 are sequentially arranged in an inflow direction of the nanoparticles caused by the respiration operating unit 200 in descending order of lattice spacing sizes thereof.

More specifically, the mesh tissue panels 300 may be formed in the mesh lattice form and the lung cell C may be attached to each of the lattice lines 301. The mesh tissue panels 300 may be formed such that the lung cell C of the human or the animal is uniformly cultivated on the respective lattice lines 301. Since a method of cultivating and attaching a cell as described above is achieved through various known cell cultivating methods, detailed descriptions thereof will be omitted.

The mesh tissue panels 300 are mounted in plural and formed to have the different lattice spacings $d_1$, $d_2$, $d_3$, and $d_4$. The mesh tissue panels 300 are sequentially arranged in the inflow direction of the nanoparticles in descending order of the lattice spacing sizes thereof.

That is, as described above, air and nanoparticles flow into the internal space of the case 100 from the outside by the particle supply unit 210 of the respiration operating unit 200. At this time, the mesh tissue panels 300 are sequentially arranged in the inflow direction of the nanoparticles in descending order of the lattice spacing sizes thereof as illustrated in FIGS. 2 and 3. For example, four mesh tissue panels 310, 320, 330, and 340 may be arranged in a line in the inflow direction of the nanoparticles as illustrated in FIGS. 2 and 3. At this time, the mesh tissue panel 310 located on an upstream side with respect to the inflow direction of the nanoparticles may have relatively large lattice spacing $d_1$, and the mesh tissue panels 320, 330, and 340 may be arranged in a line such that lattice spacings thereof are reduced in descending order of $d_2$, $d_3$, and $d_4$ toward a downstream side.

According to the structure as described above, when the nanoparticles and the air flow into the internal space of the case 100 by the respiration operating unit 200, the nanoparticles and the air sequentially pass through the plurality of mesh tissue panels 300 (310, 320, 330, and 340) in descending order of the lattice spacing sizes thereof. At this time, since the mesh tissue panel 310 located on the upstream side has the relatively large lattice spacing d1, relatively large amounts of the nanoparticles pass through the mesh tissue panel 310. However, since the mesh tissue panels 320, 330, and 340 located on the downstream side have the lattice spacings d2, d3, and d3 sequentially reduced, amounts of the nanoparticles passing through the mesh tissue panels 320, 330, and 340 are sequentially reduced.

That is, while the nanoparticles flowing into the internal space of the case 100 by the respiration operating unit 200 pass through the plurality of mesh tissue panels 300 (310, 320, 330, and 340), the nanoparticles pass through the plurality of mesh tissue panels 300 (310, 320, 330, and 340) in a state in which a portion of the nanoparticles is attached to each of the plurality of mesh tissue panels 300 (310, 320, 330, and 340). In particular, since the plurality of mesh tissue panels 300 (310, 320, 330, and 340) have the lattice spacings sequentially reduced, through amounts of the nanoparticles are further reduced while the nanoparticles are passing through the mesh tissue panels 300 (310, 320, 330, and 340).

In addition, since it is difficult for relatively large nanoparticles to pass through the mesh tissue panels 300, it is easy for the relatively large nanoparticles to be attached to the mesh tissue panel 300 located on the upstream side. However, since it is relatively easy for relatively small nanoparticles to pass through the mesh tissue panels 300, the relatively large nanoparticles may reach and be attached to the mesh tissue panels 300 located on the downstream side.

As described above, a placement structure of the mesh tissue panels 300 is similar to a structure of the lung. As described above, air in the inhalation process of the respiration operation is inhaled into the trachea, the bronchial tube, the bronchial branch, and the alveolus. The trachea, the bronchial tube, the bronchial branch, and the alveolus sequentially constitute more fine tissues. In the same manner as described above, according to an embodiment of the present disclosure, the mesh tissue panels 300 are arranged in the inflow direction of the nanoparticles in descending order of the lattice spacing sizes thereof.

According to the structure as described above, the lung model device according to the present disclosure may have a structure similar to a structure of actual lungs. The lung model device may perform the respiration operation through such a structure by using the respiration operating unit 200, so that the lung model device is formed in a shape very similar to a structure and a function of actual lungs. That is, the lung model device according to the embodiment of the present disclosure may have the structure similar to the structure of actual lungs through the plurality of mesh tissue panels 300, perform a respiration function of the lungs through the respiration operating unit 200, and be formed in the shape very similar to the structure and the function of actual lungs, thereby allowing for various test methods to be carried out using the lung model device.

In particular, since the lung cell C is attached to the mesh tissue panels 300, the inhalation toxicity test on the nanoparticles may be performed without a laboratory animal through a method of determining a change in a state of the lung cell C according to the inhalation of the nanoparticles.

For example, the four mesh tissue panels 300 may be provided as described above, and a trachea cell, a bronchial tube cell, a bronchial branch cell, and an alveolus cell may be sequentially cultivated and attached to the four mesh tissue panels 300, respectively. The mesh tissue panels 300 may represent trachea tissue, bronchial tube tissue, bronchial branch tissue, and alveolus tissue, respectively. When the aforementioned mesh tissue panels 300 are mounted in the internal space of the cover 100 and air and nanoparticles flow into the internal space of the case 100 through the respiration operating unit 200, a lung tissue cell of the mesh tissue panels 300 may be damaged by the inhaled and attached nanoparticles. The inhalation toxicity test on the nanoparticles may be performed through a method of checking the damage and an activated state of the lung tissue.

Meanwhile, the lung tissue may be various tissues such as an alveolar duct and an alveolar saccule in addition to the four previously mentioned types of tissue. For example, the lung tissue may be divided into 23 types of sub lung tissue. Cells of various sub lung tissues may be respectively cultivated and attached to the lattice lines 301 of the mesh tissue panels 300 and the number and the types of cell tissues of the mesh tissue panels 300 may be variously changed according to a user's needs.

Next, a configuration of the respiration operating unit 200 performing the respiration function of the lung will be described in more detail.

The respiration operating unit 200 alternately and repeatedly performs an air inflow and discharge operation with respect to the internal space of the case 100, and includes the particle supply module 210 allowing the nanoparticles and the air to flow into the internal space of the case 100 by generating the nanoparticles and the air discharge module 220 discharging air from the internal space of the case 100. At this time, the particle supply module 210 and the air discharge module 220 alternately and repeatedly operate.

According to the structure as described above, the nanoparticles and the air flow into the internal space of the case 100 through the particle supply module 210, and the air is discharged to the outside through the air discharge unit 220 after the inflow. The nanoparticles may be discharged together with the air while the air is being discharged through the air discharge module 220.

That is, the nanoparticles flow into the internal space of the case 100 together with the air through the particle supply module 210 and pass through the plurality of mesh tissue panels 300 while flowing into the internal space. In the process, a portion of the nanoparticles may be attached to each lung cell C attached to each of the plurality of mesh tissue panels 300 as described above. As described above, since a partial amount of the nanoparticles is attached to the lung cell C of the mesh tissue panels 300 while flowing into the internal space, a portion of the nanoparticles attached to the lung cell C is not discharged and remains as it is in the state of being attached to the lung cell C in a subsequent process of discharging the air through the air discharge module 220. Of course, remaining nanoparticles, not attached to the lung cell C, may be discharged to the outside in the process of discharging the air.

Therefore, since the respiration operating unit 200 operates and the nanoparticles repeatedly flow into the internal space of the case 100 to be attached to the lung cell C of the mesh tissue panels 300, amounts of the nanoparticles attached to the lung cell C are increased after a long time elapses. Accordingly, the lung cell C may be damaged or die. Toxicity evaluation of the nanoparticles may be performed by determining a change in characteristics of the lung cell C.

The particle supply module 210 may include a particle generator 211 generating nanoparticles and an air inflow pump 212 allowing air to flow into the internal space of the case 100 such that the nanoparticles generated from the particle generator 211 flow into the internal space of the case 100 together with the air. At this time, as illustrated in FIG. 3, the nanoparticles generated from the particle generator 211 may flow into a separate mixing chamber 213, be mixed with the air flow caused by the air inflow pump 212 in the separate mixing chamber 213, and flow into the internal space of the case 100.

The air discharge module 220 includes a buffer bag 221 mounted so as to communicate with the internal space of the case 100. The buffer bag 221 is disposed such that the air flowing into the internal space of the case 100 through the particle supply module 210 passes through the plurality of mesh tissue panels 300, and then, flows into the buffer bag 221.

That is, the buffer bag 221 is mounted so as to communicate with a lower end portion of the case 100 such that air flows into an upper portion of the internal space of the case 100 with respect to a direction shown in FIG. 4, passes through the plurality of mesh tissue panels 300, and then, flows into the buffer bag 221.

Therefore, since the air and the nanoparticles flowing into the space of the case 100 through the particle supply module 210 pass through the mesh tissue panel 300, and then, flow into the buffer bag 221, the flow of the air and the nanoparticles is reliably maintained in a manner passing through all of the plurality of mesh tissue panels 300.

Meanwhile, the buffer bag 221 may be formed of an elastic material such that a shape thereof is restored and may be formed to have an air balloon shape. Accordingly, when an operation of the particle supply module 210 is completed and the inflow of the air stops, as illustrated in FIG. 5, air is discharged to the outside from the buffer bag 221 and the internal space of the case 100 by an elastic restoring force of the buffer bag 221.

The air discharge module 220 may be formed in a shape including the buffer bag 221 formed of the elastic material. In addition to the buffer bag 221, the air discharge module 220 may further include an air discharge pump (not shown) discharging air from the internal space. In this case, the buffer bag 221 does not need to be formed of the elastic material. It may be sufficient that the buffer bag 221 is formed of a ductile material, a volume of which is simply changeable.

In addition, since the buffer bag 221 is formed to communicate with the internal space of the case 100 such that a volume thereof is changeable, the buffer bag 221 may prevent a pressure rise in the internal space of the case 100 in a process of allowing the air and the nanoparticles to flow into the internal space of the case 210 through the particle supply module 210. Accordingly, the buffer bag 221 performs a function of maintaining a smooth inflow of the air and the nanoparticles through the particle supply module 210.

On the other hand, a main pipe 410 is mounted in the case 100 to communicate with the internal space such that air flows into and from the internal space. The main pipe 410 is branched into an inflow pipe 411 and a discharge pipe 412. The inflow pipe 411 is connected to the particle supply module 210 such that the air and the nanoparticles flow into the internal space of the case 100, and the discharge pipe 412 is formed to have an open end such that the air is discharged from the internal space of the case 100.

At this time, as illustrated in FIG. 3, a channel conversion valve 420 may be mounted at a branched portion of the main pipe 410 to selectively open the inflow pipe 411 and the discharge pipe 412. The channel conversion valve 420 operates in a state of being interlocked with an operating state of the particle supply module 210 and an operating state of the air discharge nodule 220. That is, the channel conversion valve 420 operates to open the inflow pipe 411 while the particle supply module 210 is operating and operates to open the discharge valve 412 while the air discharge module 220 is operating.

According to the structure as described above, the air and the nanoparticles supplied from the particle supply module 210 flow into the internal space of the case 100 through the inflow pipe 411 and the main pipe 410 as illustrated in FIG. 4, sequentially pass through the plurality of mesh tissue panels 300 from the internal space of the case 100, and then, flow into the buffer bag 221. As described above, in the inflow process of the air and the nanoparticles, the nanoparticles are attached to the lung cell C of the mesh tissue panels 300. Thereafter, when the operation of the particle supply module 210 is completed, as illustrated in FIG. 5, air is discharged from the internal space of the case 100 by the elastic restoring force of the buffer bag 221. The discharged air is discharged from the internal space of the case 100 through the main pipe 410 and the discharge pipe 412.

The inhalation toxicity test on the nanoparticles may be performed by allowing the nanoparticles to continuously flow into the internal space of the case 100, and then, checking a change in characteristics of the lung cell C attached to the mesh tissue panels 300 by repeatedly performing the aforementioned processes.

The foregoing descriptions of specific exemplary embodiments of the present disclosure have been presented with respect to the drawings. They are not intended to be exhaustive or to limit the present disclosure to the precise forms disclosed, and obviously many modifications and variations are possible for a person having ordinary skill in the art in light of the above teachings.

It is intended therefore that the scope of the present disclosure not be limited to the foregoing embodiments, but be defined by the Claims appended hereto and their equivalents.

The foregoing descriptions have been presented in order to illustrate the certain principles of the present disclosure. A person skilled in the art to which the disclosure relates could make many modifications and variations without departing from the principle of the disclosure. The foregoing embodiments disclosed herein shall be interpreted as illustrative only but not as limitative of the principle and scope of the disclosure. It should be understood that the scope of the disclosure shall be defined by the appended Claims and all of their equivalents fall within the scope of the disclosure.

The invention claimed is:

1. A lung model device for inhalation toxicity testing, comprising:
   a case having an internal space formed therein wherein air and nanoparticles are allowed to flow into and from the internal space;
   mesh tissue panels mounted in plural in the internal space of the case, having different lattice spacings, and having lattice lines to which lung cells of a human or an animal are attached,
   wherein the plurality of mesh tissue panels are sequentially arranged in the internal space of the case in an inflow direction of the nanoparticles in descending order of sizes of the different lattice spacings thereof.

2. The lung model device of claim 1, further comprising:
   a respiration operating unit allowing the air and the nanoparticles to flow into the internal space of the case by alternately and repeatedly performing an inflow operation and a discharge operation on the air with respect to the internal space of the case; and a pipe to communicate the respiration operating unit with the internal space, wherein the respiration operating unit comprises:

a particle supply module allowing nanoparticles and air to flow into the internal space of the case by generating the nanoparticles; and an air discharge module discharging air from the internal space of the case, wherein the particle supply module and the air discharge unit alternately and repeatedly operate.

3. The lung model device of claim 2, wherein the particle supply module comprises:

a particle generator generating nanoparticles; and an air inflow pump allowing air to flow into the internal space of the case such that the nanoparticles generated by the particle generator flow into the internal space of the case together with the air.

4. The lung model device of claim 3, wherein the plurality of mesh tissue panels are formed such that the lung cells of the human or the animal are uniformly cultivated on the lattice lines of each of the plurality of mesh tissue panels.

5. The lung model device of claim 4, wherein the plurality of mesh tissue panels are provided as at least four mesh tissue panels having different lattice spacings, and a trachea cell, a bronchial tube cell, a bronchial branch cell, and an alveolus cell of the lung cells in the human or the animal are respectively cultivated on the at least four mesh tissue panels having different lattice spacings.

6. The lung model device of claim 2, wherein the air discharge module comprises a buffer bag communicating with the internal space of the case such that the air flowing into the internal space of the case through the particle supply module passes through the plurality of mesh tissue panels, and then, flows into the buffer bag, the buffer bag is formed of an elastic material such that a shape thereof is restored, and the air flowing into the internal space of the case is discharged from the internal space of the case by elastic restoring force of the buffer bag.

7. The lung model device of claim 6, wherein the plurality of mesh tissue panels are formed such that the lung cells of the human or the animal are uniformly cultivated on the lattice lines of each of the plurality of mesh tissue panels.

8. The lung model device of claim 7, wherein the plurality of mesh tissue panels are provided as at least four mesh tissue panels having different lattice spacings, and a trachea cell, a bronchial tube cell, a bronchial branch cell, and an alveolus cell of the lung cells in the human or the animal are respectively cultivated on the at least four mesh tissue panels having different lattice spacings.

9. The lung model device of claim 2, wherein the air discharge module comprises:

a buffer bag communicating with the internal space of the case such that the air flowing into the internal space of the case through the particle supply module passes through the plurality of mesh tissue panels, and then, flows into the buffer bag; and an air discharge pump discharging air from the internal space of the case.

10. The lung model device of claim 9, wherein the plurality of mesh tissue panels are formed such that the lung cells of the human or the animal are uniformly cultivated on the lattice lines of each of the plurality of mesh tissue panels.

11. The lung model device of claim 10, wherein the plurality of mesh tissue panels are provided as at least four mesh tissue panels having different lattice spacings, and a trachea cell, a bronchial tube cell, a bronchial branch cell, and an alveolus cell of the lung cells in the human or the animal are respectively cultivated on the at least four mesh tissue panels having different lattice spacings.

12. The lung model device of claim 2, wherein:

the pipe includes a main pipe which is mounted in the case to communicate with the internal space such that air flows into and from the internal space, and the main pipe is branched into an inflow pipe and a discharge pipe;

the inflow pipe is connected to the particle supply module such that the air and the nanoparticles flow into the internal space of the case; and the discharge pipe is formed to have an open end such that air is discharged from the internal space of the case.

13. The lung model device of claim 12, wherein the plurality of mesh tissue panels are formed such that the lung cells of the human or the animal are uniformly cultivated on the lattice lines of each of the plurality of mesh tissue panels.

14. The lung model device of claim 13, wherein the plurality of mesh tissue panels are provided as at least four mesh tissue panels having different lattice spacings, and a trachea cell, a bronchial tube cell, a bronchial branch cell, and an alveolus cell of the lung cells in the human or the animal are respectively cultivated on the at least four mesh tissue panels having different lattice spacings.

15. The lung model device of claim 12, wherein a channel conversion valve is mounted at a branched portion of the main pipe to selectively open the inflow pipe and the discharge pipe, and operates in a state of being interlocked with an operating state of the particle supply module and an operating state of the air discharge nodule.

16. The lung model device of claim 15, wherein the plurality of mesh tissue panels are formed such that the lung cells of the human or the animal are uniformly cultivated on the lattice lines of each of the plurality of mesh tissue panels.

17. The lung model device of claim 2, wherein the plurality of mesh tissue panels are formed such that the lung cells of the human or the animal are uniformly cultivated on the lattice lines of each of the plurality of mesh tissue panels.

18. The lung model device of claim 17, wherein the plurality of mesh tissue panels are provided as at least four mesh tissue panels having different lattice spacings, and a trachea cell, a bronchial tube cell, a bronchial branch cell, and an alveolus cell of the lung cells in the human or the animal are respectively cultivated on the at least four mesh tissue panels having different lattice spacings.

19. The lung model device of claim 1, wherein the plurality of mesh tissue panels are formed such that the lung cells of the human or the animal are uniformly cultivated on the lattice lines of each of the plurality of mesh tissue panels.

20. The lung model device of claim 19, wherein the plurality of mesh tissue panels are provided as at least four mesh tissue panels having different lattice spacings, and a trachea cell, a bronchial tube cell, a bronchial branch cell, and an alveolus cell of the lung cells in the human or the animal are respectively cultivated on the at least four mesh tissue panels having different lattice spacings.

\* \* \* \* \*